United States Patent
Fukuda

(10) Patent No.: US 9,949,625 B2
(45) Date of Patent: Apr. 24, 2018

(54) ELECTRONIC ENDOSCOPE

(71) Applicant: HOYA CORPORATION, Tokyo (JP)

(72) Inventor: Masaaki Fukuda, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 799 days.

(21) Appl. No.: 14/140,131

(22) Filed: Dec. 24, 2013

(65) Prior Publication Data
US 2014/0187867 A1    Jul. 3, 2014

(30) Foreign Application Priority Data
Dec. 28, 2012    (JP) .................... 2012-287616

(51) Int. Cl.
*A61B 1/06* (2006.01)
*A61B 1/04* (2006.01)
*H04N 5/225* (2006.01)

(52) U.S. Cl.
CPC ............. *A61B 1/0646* (2013.01); *A61B 1/04* (2013.01); *H04N 5/2252* (2013.01); *H04N 5/2254* (2013.01); *H04N 5/2257* (2013.01)

(58) Field of Classification Search
CPC ...... A61B 1/04; A61B 1/0646; H04N 5/2252; H04N 5/2254; H04N 5/2257
(Continued)

(56) References Cited
U.S. PATENT DOCUMENTS 4,621,284 A * 11/1986 Nishioka ............ A61B 5/1076
                                                        348/135
4,713,683 A * 12/1987 Fujimori ............ A61B 1/0638
                                                        348/269
(Continued)

FOREIGN PATENT DOCUMENTS

CN    101400294    4/2009
CN    102525375    7/2012
(Continued)

OTHER PUBLICATIONS

Masukawa et al., "Light Source Device for Electronic Endoscope", JP2011-200377A, Oct. 13, 2011, espacenet.com, 18 pages, English machine translation.*
(Continued)

*Primary Examiner* — John P Leubecker
*Assistant Examiner* — Arnaldo Torres Diaz
(74) *Attorney, Agent, or Firm* — Greenblum & Bernstein, P.L.C.

(57) ABSTRACT

An electronic endoscope has a light source configured to emit normal light toward an object and a rotating filter configured to be positioned in the path of light that passes from the light source to an image sensor. The rotating filter has an optical band-pass filter and a ND filter. The electronic endoscope has further a rotation controller that synchronizes a light-path traverse-interval of the band-pass filter and a light-path traverse-interval of the ND filter with a field/frame interval; and an image generator that generates a normal image from broadband image-pixel signals and generates a spectral image from specific-band image-pixel signals. The image generator has a brightness adjuster that increases a brightness level of the spectral image. Then, the ND filter reduces an amount of light emitted from the light source to an amount of light that corresponds to an increased brightness of the spectral image.

5 Claims, 6 Drawing Sheets

(58) Field of Classification Search
USPC .................................................. 600/178, 181
See application file for complete search history.

(56) References Cited

U.S. PATENT DOCUMENTS

| | | | | |
|---|---|---|---|---|
| 4,983,019 | A * | 1/1991 | Ikuno | A61B 1/042 348/68 |
| 5,408,265 | A * | 4/1995 | Sasaki | A61B 1/042 348/443 |
| 5,507,287 | A * | 4/1996 | Palcic | A61B 1/00186 356/318 |
| 6,471,636 | B1 * | 10/2002 | Sano | A61B 1/00186 348/65 |
| 6,902,527 | B1 * | 6/2005 | Doguchi | A61B 1/00059 348/65 |
| 7,172,553 | B2 * | 2/2007 | Ueno | A61B 1/00009 600/109 |
| 7,258,663 | B2 * | 8/2007 | Doguchi | A61B 1/00059 348/65 |
| 7,704,206 | B2 * | 4/2010 | Suzuki | A61B 1/043 348/70 |
| 7,892,169 | B2 * | 2/2011 | Gono | A61B 1/0638 348/70 |
| 8,167,796 | B2 * | 5/2012 | Negishi | A61B 1/0669 362/574 |
| 8,419,633 | B2 * | 4/2013 | Koshikawa | A61B 1/0638 362/574 |
| 8,531,512 | B2 | 9/2013 | Gono et al. | |
| 8,537,210 | B2 * | 9/2013 | Omori | A61B 1/00059 348/68 |
| 9,084,557 | B2 * | 7/2015 | Masaki | A61B 1/0646 |
| 2003/0176768 | A1 * | 9/2003 | Gono | A61B 1/0638 600/109 |
| 2007/0088193 | A1 * | 4/2007 | Omori | A61B 1/00059 600/101 |
| 2007/0093691 | A1 * | 4/2007 | Kobayashi | A61B 1/00009 600/180 |
| 2007/0123751 | A1 | 5/2007 | Takahashi | |
| 2008/0249368 | A1 * | 10/2008 | Takei | A61B 1/00009 600/178 |
| 2013/0158352 | A1 * | 6/2013 | Imaizumi | A61B 1/00009 600/111 |

FOREIGN PATENT DOCUMENTS

| | | |
|---|---|---|
| CN | 102551642 | 7/2012 |
| CN | 102695446 | 9/2012 |
| CN | 102753083 | 10/2012 |
| JP | 2002-34893 | 2/2002 |
| JP | 2002-95635 | 4/2002 |
| JP | 2002-112960 | 4/2002 |
| JP | 2004-321244 | 11/2004 |
| JP | 2005-261974 | 9/2005 |
| JP | 2006-218283 | 8/2006 |
| JP | 2006-314629 | 11/2006 |
| JP | 2007-111328 | 5/2007 |
| JP | 2007-167325 | 7/2007 |
| JP | 2007-300972 | 11/2007 |
| JP | 2008-023101 | 2/2008 |
| JP | 2009-225831 | 10/2009 |
| JP | 2011-200377 | 10/2011 |
| JP | 2011-200417 | 10/2011 |
| WO | 2007/129570 | 11/2007 |

OTHER PUBLICATIONS

Chinese Office Action for CN App. No. 201310741551.9 dated May 24, 2016, along with English-language translation thereof.

Japanese Office Action for JP App. No. 2012-287616 dated Nov. 29, 2016, along with an English-language translation thereof.

* cited by examiner

<N.O. MODE>

<S.O. MODE>

<S.D. MODE>

|  | W.L. | N.L. |
|---|---|---|
| W.I.V. | 100% | 20% |
| TRANS. | 50% | 100% |
| GAIN VALUE | 1 | 2.5 |

ELECTRONIC ENDOSCOPE

BACKGROUND OF THE INVENTION

1. Field of the Invention

The present invention relates to an electronic endoscope that is capable of photographing an organ in a body, and it especially relates to a display of a spectral image obtained by emitting light having specific wavelengths.

2. Description of the Related Art

In an electronic endoscope, a color image is displayed by emitting a white light toward an object to be observed, and a spectral image with a color that is different from a normal image color can be also displayed by emitting light with a restricted bandwidth of wavelengths, such as ultraviolet rays, infrared rays, and so on. For example, a rotary filter in which an ND (Neutral Density) filter and an optical band-pass filter are formed circumferentially is arranged in an endoscope processor. The ND filter reduces the intensity or amount of all wavelengths of visible light equally when the visible light passes through the ND filter, whereas the band-pass filter blocks all light except for light having specific wavelengths. The rotary filter rotates in accordance to one field/frame interval. JP2011-200377A1 discloses such a rotating filter plate. Thus, image-pixel signals corresponding to normal white light and image-pixel signals corresponding to narrow-band light are read out from an image sensor alternately, and two images may be displayed on a screen in real time. An amount of light passing through the band-pass filter decreases compared to the same amount of light that enters the band-pass filter. To display a normal color image and a spectral image with the same brightness level, an amount of normal white light is reduced by a predetermined transmittance of the ND filter.

When the transmittance of the ND filter depends upon the amount of light that passes through the band-pass filter, the brightness of the normal observation image may not be sufficient for observation. And especially when an auto-brightness process is performed in accordance to a luminance level of the normal observation image, an aperture should be opened wider than usual, which could cause difficulty in the auto-brightness process.

SUMMARY OF THE INVENTION

An object of the present invention is to provide an electronic endoscope that displays a normal image and a spectral image with a proper brightness.

An electronic endoscope according to the present invention has a light source configured to emit normal light toward an object to be observed, the normal light having a broad band of wavelengths; and a rotating filter configured to be positioned in the path of light that passes from the light source to an image sensor, and have an optical band-pass filter and a ND (Neutral Density) filter that are arranged circumferentially; a rotation controller that synchronizes a light-path traverse-interval of the band-pass filter and a light-path traverse-interval of the ND filter with a field/frame interval; and an image generator that generates a normal image from broadband image-pixel signals and generates a spectral image from specific-band image-pixel signals. The broadband image-pixel signals and the specific-band image-pixel signals are read from an image sensor alternately. The image generator has a brightness adjuster that increases a brightness level of the spectral image. Then, the ND filter reduces an amount of light emitted from the light source to an amount of light that corresponds to an increased brightness of the spectral image.

A transmittance of the ND filter may be larger than a transmittance corresponding to a ratio of the spectral wavelength integral value of light passing through the band-pass filter to a standard wavelength integral value of normal light. The brightness adjuster may perform a gain process by a given gain value. The transmittance may be set to a value corresponding to a gain value that changes the brightness of the normal image to coincide with the brightness of the corrected spectral image. A display processor that displays a normal image and a spectral image on a screen simultaneously may be provided. Also, an auto-brightness adjustment processor may adjust the brightness of the normal image and the spectral image on the basis of the brightness of the normal image may be provided.

A rotary filter for endoscope according to another aspect of the present invention has a rotary filter for endoscope, comprising: a disk-shaped rotating member; a ND filter; and an optical band-pass filter. The optical band-pass filter and the ND (Neutral Density) filter are arranged on the rotating member circumferentially. The ND filter has a transmittance that reduces an amount of light emitted from the light source to an amount of light that corresponds to the brightness of the spectral image that is increased by a gain process.

BRIEF DESCRIPTION OF THE DRAWINGS

The present invention will be better understood from the description of the preferred embodiments of the invention set forth below together with the accompanying drawings, in which.

DESCRIPTION OF THE PREFERRED EMBODIMENTS

Hereinafter, the preferred embodiment of the present invention is described with reference to the attached drawings.

Hereinafter, the preferred embodiment of the present invention is described with reference to the attached drawings.

Figure 1:
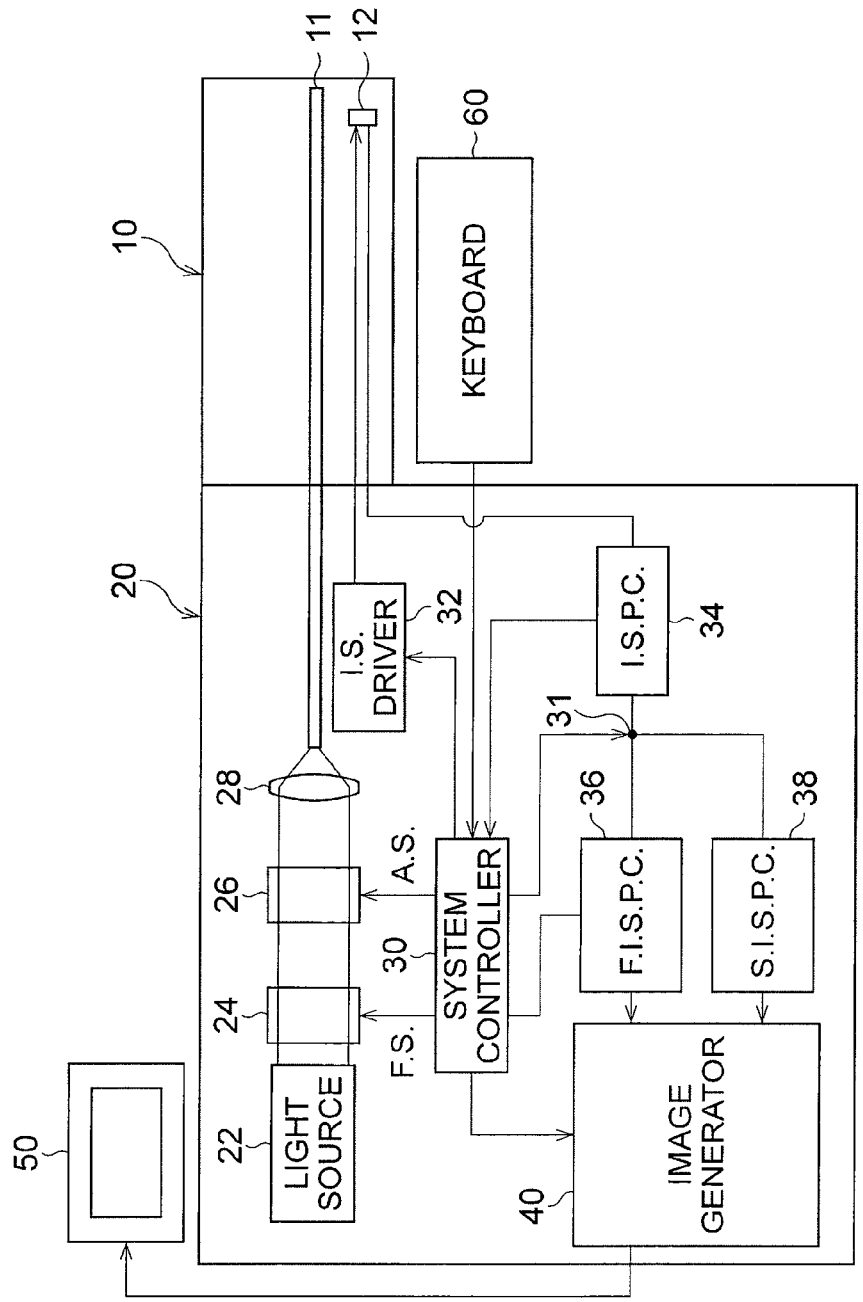
FIG. 1 is a block diagram of an electronic endoscope according to the preferred embodiments.
Figure 2A:
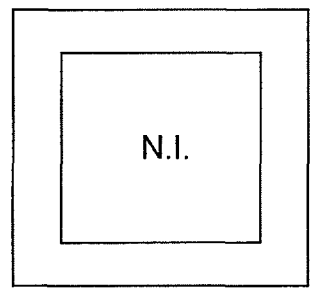
FIG. 2A is a view showing a screen in a normal observation mode.
Figure 2B:
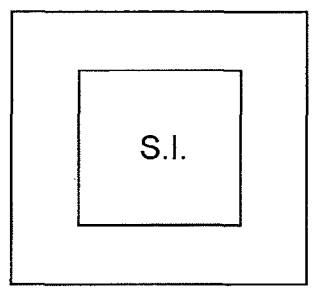
FIG. 2B is a view showing a screen in a special observation mode.
Figure 2C:
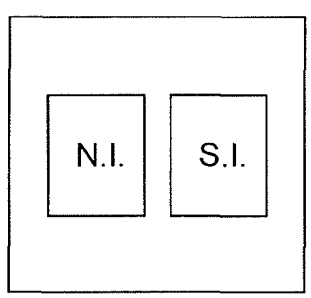
FIG. 2C is a view showing a screen in a simultaneous observation mode.

FIG. 1 is a block diagram of an electronic endoscope according to the embodiment. FIG. 2A is a view showing a screen in a normal observation mode. FIG. 2B is a view showing a screen in a special observation mode. FIG. 2C is a view showing a screen in a simultaneous observation mode.

An electronic endoscope is equipped with a video scope 10 having an image sensor 12 such as a CCD or CMOS, and a video processor 20. The video scope 10 is detachably connected to the video processor 20, and a monitor 50 and a keyboard 60 are connected to the video processor 20.

The video-processor 20 is equipped with a light source 22 such as a discharge lamp, which emits white light. Light emitted from the light source 22 passes through a collecting lens 28, and passes through an incident surface (not shown) of a light guide 11 provided in the video scope. The light guide 11, composed of a fiber-optic bundle, directs the light to the tip portion of the video scope 10. The light passing through the light guide 11 emerges through the tip of the light guide 11 and exits from the tip of the video scope 10 via a diffusion lens (not shown), so that a subject to be observed may be illuminated.

Light reflected off the subject passes through an objective lens (not shown) and reaches the image sensor 12, so that an object image is formed on a photo-sensor area of the image sensor 12. On the photo-sensor area of the CCD 12 is a color filter array (not shown), which is checkered by color elements including Yellow (Y), Magenta (Mg), Cyan (Cy), and Green (G); or Red (R), Green (G) and Blue (B); and is arranged such that each area of the color elements is opposite a pixel.

In the image sensor 12, analog image-pixel signals are generated by the photoelectric effect, based on light passing through the color filter. An image sensor driver 32 outputs clock pulse signals to the image sensor 12 so that the image-pixel signals are read from the image sensor 12 at regular time intervals. For example, in the case where the NTSC or PAL standard is applied, one field's worth of image-pixel signals are read from the image sensor 12 successively at 1/60- or 1/50-second time intervals. The image-pixel signals are fed to an initial signal-processing circuit 34.

In the initial signal-processing circuit 34, signal processing including an A/D conversion process and color interpolation process is performed on the image-pixel signals so that a series of R, G, and B image-pixel signals are generated. The generated R, G, and B image-pixel signals are fed to a first image-signal processing circuit (F.I.S.P.C.) 36 and/or a second image-signal processing circuit (S.I.S.P.C.) 38. In the first and/or second image signal-processing circuit 36 and/or 38, various processes including a white-balance adjustment process, a color conversion process, a gain process and a gamma-correction process are performed on the R, G, and B image-pixel signals, so that one field/frame worth of R, G, and B image signals are generated successively and are directly output to the monitor 50. Thus, a full-color moving image is displayed on the monitor 50.

A system controller 30 including a CPU (not shown), ROM unit and RAM unit controls the video processor 20, and outputs control signals to circuits in the video processor 20. An operator may operate an observation switch button (not shown) provided on the front panel of the video processor 20 during the use of the electronic endoscope. The observation switch button switches an observation mode between a normal observation mode, special observation (spectral image) mode, or simultaneous display (twin) mode.

As shown in FIG. 2A, in the normal observation mode, the object is illuminated with white light (normal light) having a broad band of wavelengths. Thus, a normal full color image is displayed. On the other hand, in the special observation mode, the object is illuminated with light having a specific band of wavelengths (narrow-band light; see FIG. 2B). Thus, a spectral image of a clear blood vessel image can be displayed. In the case of the simultaneous display mode, white light and narrow-band light are illuminated alternately, and a normal color image and a spectral image are displayed on the screen in real time (see FIG. 2C).

A stop mechanism 26 provided between the light source 22 and the condenser lens 28 increases or decreases an amount of light by its open-close motion. The system controller 30 performs an auto-brightness adjustment process at field/frame intervals to obtain the proper brightness of a displayed observation image. Concretely, the system controller 30 outputs control signals to the stop mechanism 26 based on luminance signals successively fed from the initial signal-processing circuit 34. Note that, in the case of the simultaneous display mode, the brightness adjustment process is performed on the basis of luminance signals obtained from image-pixel signals generated by white light.

A rotary filter mechanism 24 is provided between the light source 22 and the stop mechanism 26 and is equipped with a rotary filter (herein, not shown). The rotary filter is selectively positioned on a light-path or outside of the light-path. The rotation speed or phase of the rotary filter is controlled by the 30.

Figure 3:
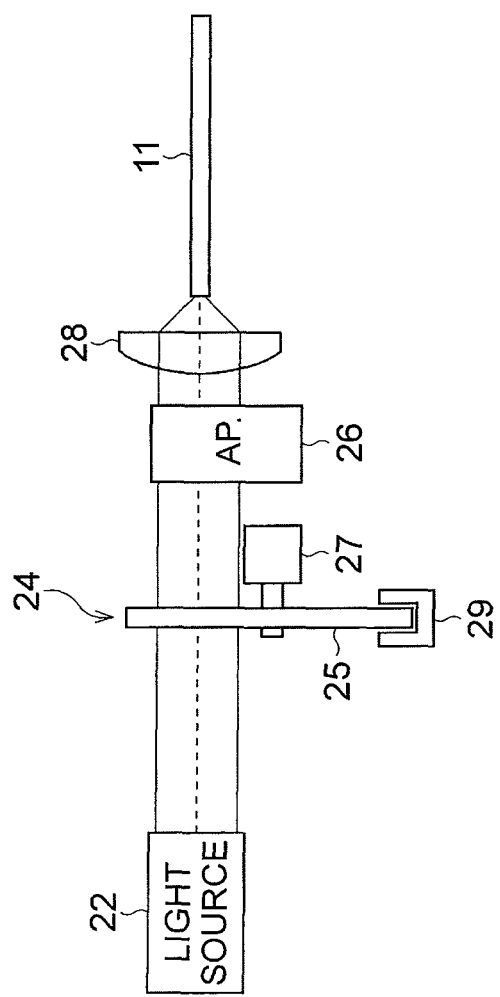
FIG. 3 is a view showing an arrangement of the rotary filter.
Figure 4:
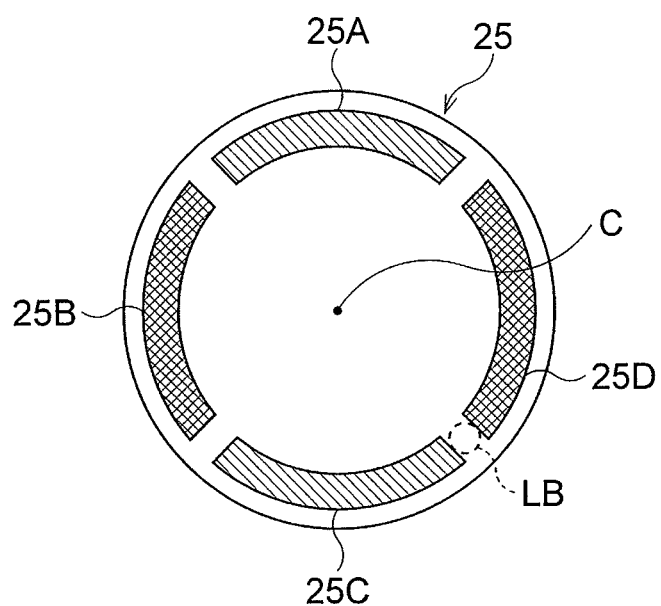
FIG. 4 is a front view of the rotary filter.

FIG. 3 is a view showing an arrangement of the rotary filter. FIG. 4 is a front view of the rotary filter. With reference to FIGS. 3 and 4, the rotary filter is explained in detail.

The disk-shaped rotary filter 25 is rotated around an axis C by a motor 27, and an encoder 29 is provided adjacent to the limb of the rotary filter 25. Also, the rotary filter 25 may be moved between a position directly in line with the light-path and a position outside of the light-path, along a direction perpendicular to the optical axis, by a support member (not shown).

In the normal observation mode, the rotary filter 25 is positioned outside of the light-path. Thus, white light emitted from the light source 22 directly enters into the light guide 11. In the case of the special observation mode and the simultaneous display mode, the rotary filter 25 is moved into the light-path and rotated.

The rotary filter 25 has a pair of arc-shaped band-pass filters 25A and 25C and a pair of arc-shaped ND filters 25B and 25D, which are disposed alternately along a circumferential direction and are opposite to one another. Each filter has a circumferential length of one quadrant.

In the special observation mode, the rotary filter 25 is positioned at the location where the light-path LB passes through the band-pass filter 25A or 25C, without rotation. On the other hand, in the case of the simultaneous display mode, the rotary filter 25 is positioned at the location where the light-path LB passes through the band-pass filters 25A and 25C and the ND filters 25B and 25D during rotation. The rotation speed and the phase of the rotary filter 25 are controlled such that the rotary filter 25 rotates by one quarter during one field interval.

The band-pass filters 25A and 25C have spectral distribution characteristics that allow a part of the white light that has specific wavelengths to pass through the band-pass filters 25A and 25C. All of wavelengths of the visible light passes through the ND filters 25B and 25D, however, the ND filters 25B and 25D reduce the intensity or amount of all wavelengths of visible light equally. The ND filters 25B and 25D are formed with a film or metal mesh.

In the simultaneous display mode, a light-path crossing interval of one band-pass filter or ND filter is synchronized with one field interval by controlling the rotation speed and the phase of the rotary filter 25. Consequently, one field worth of image-pixel signals corresponding to white light and one field worth of image-pixel signals corresponding to narrow-band light are alternately read from the image sensor 12.

The system controller 30 controls a switch 31 to send a series of R, G, and B image-pixel signals generated by white light and a series of R, G, and B image-pixel signals generated by narrow-band light to the F.I.S.P.C. 36 and the S.I.S.P.C 38 alternately.

Figure 5:
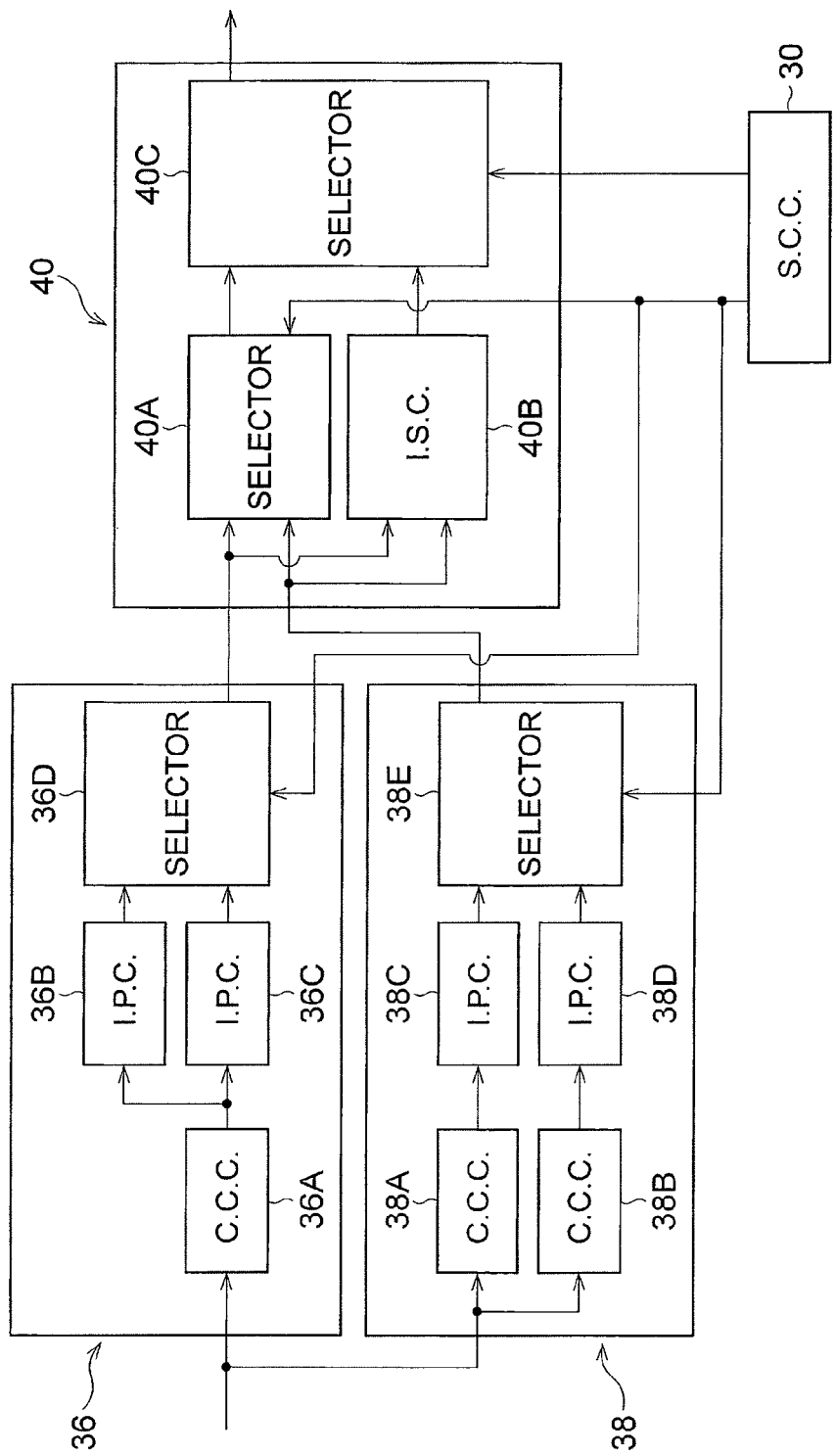
FIG. 5 is a block diagram of a F.I.S.P.C., S.I.S.P.C, and an image generator.

FIG. 5 is a block diagram of the F.I.S.P.C. 36, the S.I.S.P.C 38, and the image generator 40.

The F. I. S. P. C. 36, which receives the series of R, G, and B image-pixel signals based on the white light, is equipped with a color conversion circuit 36A, image processing circuits 36B and 36C, and a selector 36D. In the color conversion circuit 36A, luminance signals and color difference signals corresponding to a normal color image signal are generated.

The image processing circuits 36B and 36C perform an edge enhancement process and so on. In the normal observation mode, the selector 36D selects the image signals output from the image processing circuit 36B and send them to the image generator 40. In the simultaneous display mode, the selector 36D selects the image signals output from the image processing circuit 36C.

The S. I. S. P. C. 38, which receives the series of R, G, and B image-pixel signals based on the narrow-band light, is equipped with color conversion circuits 38A and 38B, image processing circuits 38C and 36D, and a selector 38E. In the color conversion circuits 38A and 38B, luminance signals and color difference signals based on narrow-band light signals are generated.

In the special observation mode, the selector 38E selects the image signals generated by the image processing circuit 38C and sends them to the image generator 40. In the simultaneous display mode, the selector 38E selects the image signals generated by the color conversion circuit 38B and the image processing circuit 38D. In the image processing circuit 38D, as described later, a gain process is performed. In the simultaneous mode, the image processing circuit 38C may perform a gain process. In this case, a gain value in the image processing circuit 38C is set to a value smaller than that in the image processing circuit 38D.

The image generator 40 has selectors 40A and 40C and an image synthesis circuit 40B. The image synthesis circuit 40B generates image signals for a normal image and image signals for a spectral image in the simultaneous display mode. In the normal observation mode or the special observation mode, the selectors 40A and 40C act such that image signals based on normal white light or image signals based on narrow-band light are output from the image generator 40. In the simultaneous display mode, the selector 400 selects the image signals output from the image synthesis circuit 40B.

Figures 6, 7:
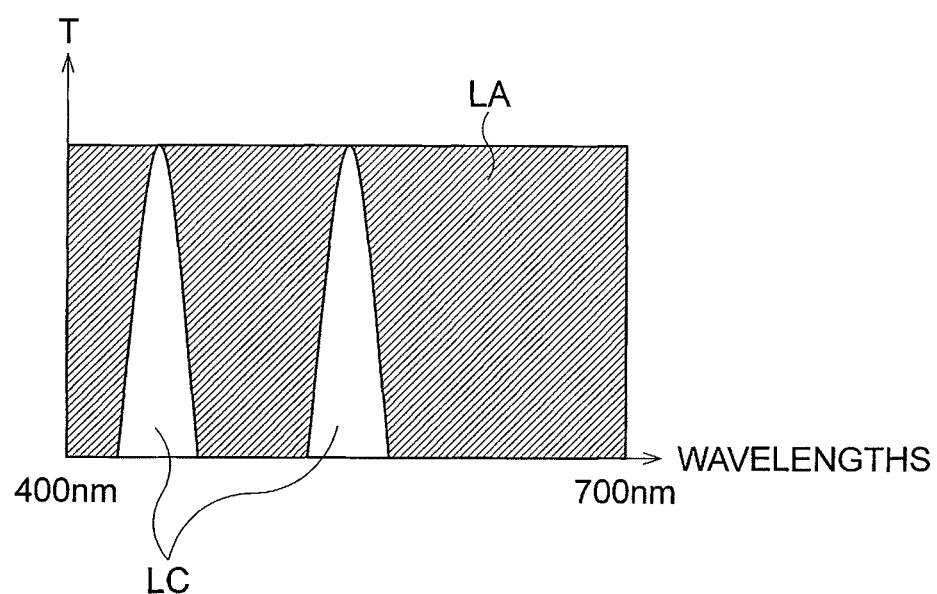
FIG. 6 is a view showing a spectral transmission of the band-pass filter.
FIG. 7 is a view showing a table indicating the relationship between transmittance of the ND filter and the gain value.

FIG. 6 is a view showing a spectral transmission of the band-pass filter. FIG. 7 is a view showing a table indicating the relationship between transmittance of the ND filter and the gain value. With reference to FIGS. 6 and 7, a brightness adjustment applied to the normal image and the spectral image in the simultaneous display mode is explained.

As shown in FIG. 6, the band-pass filter 25A of the rotary filter 25 blocks light other than narrow-band light having wavelengths of approximately 415 nm and 540 nm. Light having other wavelengths may passes through the band-pass filter 25A. The band-pass filter 25C similarly blocks light to the band-pass filter 25A.

White light has continuous and uniform spectrum distribution characteristics that cover a broad band of wavelengths. Therefore, when white light enters the band-pass filter 25A having the above spectral transmission characteristics, the entire amount or intensity of light decreases since only a part of the light passes through the band-pass filter 25A. When a spectral integral value "LA" of white light (hereinafter, called a "wavelength spectral integral value) is set to a standard value (herein, 1), the spectral integral value "LC" of light passing through the band-pass filter 25A is herein 0.2.

The spectral integral value LC is obtained by integrating a wavelength of passing light over the full spectrum of wavelengths. Therefore, when the total intensity/amount of white light is 100%, the intensity/amount of light passing through the band-pass filter 25A is 20% (see FIG. 7). Namely, the total amount of narrow-band light decreases to ⅕ of the amount of white light.

To compensate for such a decrease in the amount of light, the image signals that are obtained based on the narrow-band light undergo a gain process. This gain process does not adjust the luminance balance with respect to R, G, and B color signals, but instead increases the luminance level of the total spectral image. In addition, as for the normal observation image, the ND filter 25B or 25D reduces the white light by a given amount. Concretely, the ND filters 25B or 25D reduce the white light by an amount such that the brightness of the normal observation image and the brightness of the spectral image corrected by the gain process are substantially equal.

The gain value may be set to a value that is equal to or less than 3 (three times). This is because relatively large gain values influence image quality. Herein, the gain value is set to 2.5. Accordingly, the transmittance of the ND filters 25B and 25D is set to 50 percent, namely, the ND filters 25B and 25D reduce the total amount of white light by half. Thus, the brightness of the normal image is the same as that of the corrected brightness of the spectral image.

This transmittance of the ND filters 25B and 25D is larger than a transmittance corresponding to a ratio of the spectral wavelength integral value "LC" to the standard wavelength integral value "LA", since the brightness of the spectral image is increased by the gain process. Namely, the normal image and the spectral image can be displayed at the same brightness without a transmittance of 20 percent. Accordingly, a decrease of white light is restricted with respect to a range in which a gain process can be performed.

In this way, during the simultaneous display mode, the rotary filter 25 with the band-pass filters 25A and 25C and the ND filters 25B and 25D rotate so that white light and narrow-band light are illuminated alternately. The image signals based on the narrow-band light undergo the gain process to increases the brightness of the spectral image, whereas the brightness of normal image decreases in accordance to the transmittance of the ND filters 25B and 25D. The value of the transmittance is predetermined such that the brightness of the normal image becomes that of the corrected brightness of the spectral image.

In the present embodiment, the brightness of the normal image is reduced by decreasing an amount of illuminated light, whereas the brightness of the spectral image is increased by the image processing. Since the two different brightness adjustments are performed, the normal image with proper brightness can be displayed. The brightness of the spectral image is relatively dark compared with that of the spectral image displayed in the special observation mode, since an amount of exposure is limited due to a mechanism of the rotary filter. However, the brightness of the spectral image is corrected by the gain process, and the gain value (>1) is set to a proper value equal to or less than 3. Thus, the spectral image with a proper brightness can be displayed and an operator can diagnose using the spectral image. Furthermore, an auto-brightness adjustment process based on the brightness level of the normal image can adjust the brightness of the normal image and the spectral image precisely.

The gain value may be set to a value more than 3 in accordance to performance of the image processing circuit. Also, the brightness of the normal image may be changed to some extent such that the brightness of the normal image is roughly the same as that of the spectral image in appearance, instead of precise adjustment of the brightness. The transmittance of the ND filter may be determined based on the ratio of wavelength integral value of the narrow-band filter.

The structure of the rotary filter may be optionally designed. For example, a rotary filter with a plurality of ND filters that are arranged coaxially and have different transmittances respectively may be provided. In this case, the rotary filter is positioned in accordance to a content of diagnosis. Also, a plurality of rotary filter that have different transmittances may be provided. In this case, one rotary filter is selected in accordance to a content of diagnosis.

Finally, it will be understood by those skilled in the arts that the foregoing description is of preferred embodiments of the device, and that various changes and modifications may be made to the present invention without departing from the spirit and scope thereof.

The present disclosure relates to subject matter contained in Japanese Patent Application No. 2012-287616 (filed on Dec. 28, 2012), which is expressly incorporated herein, by reference, in its entirety.

What is claimed is:

1. An electronic endo scope comprising:
  a light source configured to emit normal light toward an object to be observed, the normal light having a broad band of wavelengths;
  a rotating filter positioned between said light source and an image sensor configured to be positioned in a path of light to filter the normal light that passes from said light source to the image sensor, and includes an optical band-pass filter and a Neutral Density filter that are arranged circumferentially;
  a rotation controller that synchronizes a light-path traverse-interval of said optical band-pass filter and a light-path traverse-interval of said Neutral Density filter with a field/frame interval; and
  an image generator that generates a normal image from broadband image-pixel signals and generates a spectral image from specific-band image-pixel signals, the broadband image-pixel signals and the specific-band image-pixel signals being read from the image sensor alternately,
  said image generator comprising a brightness adjuster that increases a brightness level of the spectral image being generated by the image generator,
  said Neutral Density filter decreases a brightness level of the normal image by reducing an amount of light emitted from said light source to an amount of light that corresponds to an increased brightness level of the spectral image,
  a transmittance of said Neutral Density filter is larger than a transmittance corresponding to a ratio of a spectral wavelength integral value of light passing through said optical band-pass filter to a standard wavelength integral value of normal light, and
  the transmittance is a value corresponding to a gain value that changes the brightness level of the normal image to coincide with a brightness level of a corrected spectral image.

2. The electronic endoscope of claim 1, wherein said brightness adjuster performs a gain process based on the gain value.

3. The electronic endoscope of claim 1, further comprising a display processor that displays the normal image and the spectral image on a screen simultaneously.

4. The electronic endoscope of claim 1, further comprising an auto-brightness adjustment processor that adjusts the brightness level of the normal image and the brightness level of the spectral image on the basis of the brightness level of the normal image.

5. A rotary filter for an endoscope, comprising:
  a single disk-shaped rotating member;
  a Neutral Density filter; and
  an optical band-pass filter,
  said optical band-pass filter and said Neutral Density filter being arranged on said rotating member circumferentially such that normal light and narrow-band light exiting the optical band-pass filter alternately illuminate an object,
  said Neutral Density filter having a transmittance that reduces an amount of light emitted from a light source such that an amount of light passing through the Neutral Density filter from the light source corresponds to a brightness level of a spectral image that is increased by a gain process,
  the transmittance of said Neutral Density filter is larger than a transmittance corresponding to a ratio of a spectral wavelength integral value of light passing through said optical band-pass filter to a standard wavelength integral value of normal light, and
  the transmittance is a value corresponding to a gain value that changes a brightness level of the normal image to coincide with a brightness level of a corrected spectral image.

* * * * *